United States Patent
Segal

(10) Patent No.: US 6,224,870 B1
(45) Date of Patent: May 1, 2001

(54) VACCINE COMPOSITIONS AND METHODS OF MODULATING IMMUNE RESPONSES

(75) Inventor: Andrew H. Segal, Boston, MA (US)

(73) Assignee: Genitrix, Ltd., Cambridge, MA (US)

( * ) Notice: Subject to any disclaimer, the term of this patent is extended or adjusted under 35 U.S.C. 154(b) by 0 days.

(21) Appl. No.: 09/007,711

(22) Filed: Jan. 15, 1998

Related U.S. Application Data

(63) Continuation-in-part of application No. 08/788,143, filed on Jan. 24, 1997, now abandoned.

(51) Int. Cl.[7] .......................... A61K 39/00; A61K 31/70; A01N 43/04

(52) U.S. Cl. .......................................... 424/192.1; 514/44

(58) Field of Search .............................. 424/192.1; 514/44

(56) References Cited

U.S. PATENT DOCUMENTS

| | | |
|---|---|---|
| 5,270,199 | 12/1993 | Ezekowitz . |
| 5,652,342 | 7/1997 | Zimmermann . |
| 5,668,255 | 9/1997 | Murphy . |
| 5,698,679 | 12/1997 | Nemazee . |

FOREIGN PATENT DOCUMENTS

WO 96/40941   12/1996   (CA) .

OTHER PUBLICATIONS

Seacrest, Science News, 147(22):343 Jun. 1995.*
Paul, Fundamental Immunology Fourth Edition, p. 981, table 4 1999.*
Blakeslee, JAMA HIV/AIDS Information Center, Dendritic ells Background Briefing, http://www.ama–asn.org/special/hiv/newsline/briefing/dendritic.htm Jan. 1998.*
Davis et al. PNAS 93:7213–7218 1996.*
Janeway et al. Immunobiology, Third Edition, Current Biology Limited, England 1997.*
Fawell, et al., PNAS, Jan. 1994, vol. 91; 664–668.
Hohmann et al., PNAS, Mar. 1995, vol. 92; 2904–2908.
International Search Report.
Alvarez–Domingues et al., 1993, Role of complement component C1q in phagocytosis of *Listeria monocytogenes* by murine macrophage–like cell lines, *Infect. Immun.* 61: 3664–3672.
Arvieux et al., 1988, Antigen–bound C3b and B4b enhance antigen–presenting cell function in activation of human T–cell clones, *Immunology* 65: 229–235.
Baier et al., 1995, Immunogenic targeting of recombinant peptide vaccines to human antigen–presenting cells by chimeric anti–HLA–DR and anti–surface–immunoglobulin D antibody Fab Fragments in vitro, *J. Virol.* 69: 2357–2365.
Becherer and Lambris, 1988, Identification of the C3b receptor–binding comain in third component of complement, *J. Biol. Chem. 263*: 14586–14591.

Berg et al., 1994, Comparing macrophages and dendritic leukocytes as antigen–presenting cells for humoral responses in vivo by antigen targeting, *Eur. J. Immunol.* 24: 1262–1268.
Carayanniotis and Barber, 1987, Adjuvant–free IgG responses induced with antigen coupled to antibodies against class II MHC,, *Nature 327*: 59–61.
Chu and Pizzo, 1993, Receptor–mediated antigen delivery into macroophages: Complexing antigen to $\alpha_2$–macroglobulin enhances presentation to T cells, *J. Immunol. 150*: 48–58.
Chu et al., 1994, Adjuvant–free in vivo targeting. Antigen delivery by alpha 2– macroglobulin enhances antibody formation, *J. Immunol. 152*: 1538–1545.
Cosio, 1984, Human fibronectin is an opsonin for IgG antibody–coated sheep erythrocytes, *J. Lab. Clin. Med. 103*: 613–619.
Czop and Austen, 1982, Augmentation of phagocytosis by a specific fibronectin fragment that links particulate activators to the fibronectin adherence receptor of human monocytes, *J. Immunol. 129*: 2678–2681.
Dempsey et al., 1996, C3d of complement as a molecular adjuvant: bridging innate and acquired immunity, *Science 271*: 348–350.
Estrada et al., 1995, Intestinal immunization of mice with antigen conjugated to anti–MHC class II antibodies, *Vaccine 13*: 901–907.
Gaither et al., 1987, The complement fragment C3d facilitates phagocytosis by monocytes, *Immunology 62*: 405–411.
Geertsma et al., 1994, Binding of surfactant protein A to C1q receptors mediates phagocytosis of *Staphylococcus aureus* by monocytes, *Am. J. Physiol. 267*: L578–L584.
Gosselin et al., 1992, Enhanced antigen presentation using human Fc gamma receptor (monocyte/macrophage)–specific immunogens, *J. Immunol. 149*: 3477–3481.
Guan et al., 1994, Cell–surface protein identified on phagocytic cells modulates the C1q–mediated enhancement of phagocytosis, *J. Immunol. 152*: 4005–4016.
Heijnen et al., 1996, Antigen targeting to myeloid–specific human FcγRI/CD64 triggers enhanced antibody responses in trangenic mice, *J. Clin. Invest. 97*: 31–338.
Holzer et al., 1984, Binding of C–reactive protein to the pneumococcal capsule or cell wall results in differential localization of C3 and stimulation of phagocytosis, *J. Immunol. 133*: 1424–1430.

(List continued on next page.)

Primary Examiner—David Saunders
Assistant Examiner—Amy DeCloux
(74) *Attorney, Agent, or Firm*—Palmer & Dodge, LLP; Kathleen M. Williams

(57) ABSTRACT

The invention provides compositions and methods for modulating immune responses in subjects. The invention is based, at least in part, on the discovery that an in-frame translation fusion of an antigen with an APC binding domain of an opsonin forms a molecule, that is, a fusion polypeptide, which when administered to a subject modulates an immune response to the antigen.

7 Claims, No Drawings

OTHER PUBLICATIONS

Inada et al., 1983, C3d receptors are expressed on human monocytes after in vitro cultivation, *Proc. Natl. Acad. Sci. U.S.A. 80*: 2351–2355.

Jacquier–Sarlin et al., 1995, Modulation of antigen processing and presentation by covalently linked complement C3b fragment, *Immunology 84*: 164–170.

Kuhlman et al., 1989, The human mannose–binding protein functions as an opsonin, *J. Exp. Med. 169*: 1733–1745.

Lambris and Ross, 1982, Assay of membrane complement receptors ($CR_1$ and $CR_2$) with C3b– and C3d–coated fluorescent microspheres, *J. Immunol. 128*: 186–189.

McHugh et al., 1995, Construction, purification, and functional incorporation on tumor cells of glycolipid–anchored human B7–1 (CD80), *Proc. Natl. Acad. Sci. U.S.A. 93*: 8059–8063.

Pikaar et al., 1995, Opsonic activities of surfactant proteins A and D in phgocytosis of gram–negative bacteria by alveolar macrophages, *J. Infect. Disease 172*: 481–489.

Simpson and Boughton, 1984, Firbonectin as an opsonic regulator of monocyte phagocytosis, *J. Clin. Pathol. 37*: 787–789.

Snider and Segal, 1989, Efficiency of antigen presentation after antigen targeting to surface IgD, IgM, MHC, Fc gamma RII, and B220 molecules on murine splenic B cells, *J. Immunol. 143*: 59–65.

Squire et al., 1994, Antigen presentation is enhanced by targeting antigen to the Fc epsilon RII by antigen–anti–Fc epsilon RII conjugates, *J. Immunol. 152*: 4388–4396.

Tebo and Mortenson, 1990, Characterization and isolation of a C–reactive protein receptor from the human moncytic cell line U–937, *J. Immunol. 144*: 231–238.

\* cited by examiner

VACCINE COMPOSITIONS AND METHODS OF MODULATING IMMUNE RESPONSES

This application is a continuation in part of U.S. Ser. No. 08/788,143 filed Jan. 24, 1997 abandoned.

FIELD OF THE INVENTION

This invention relates to vaccines useful, for example, for modulating immune responses in subjects to a variety of antigens.

BACKGROUND OF THE INVENTION

The innate immune system comprises those mechanisms that have evolved over millennia to provide first line defense against foreign antigens and an antigen recognition repertoire which does not diversify during the ontogeny of the individual. This is in contrast with the acquired immune system which provides later phase defense mechanisms and depends on a repertoire of antigen-specific molecules, e.g., immunoglobulins and T cell receptors that diversify over the ontogeny of the individual. Innate immune mechanisms can contribute to initiation of an antigen-specific response by the acquired immune system, for example by facilitating uptake of antigen by antigen-presenting cells (APCs), which can thereafter stimulate cognate T cells.

Opsonins of the innate immune system ("innate opsonins") are known in the art as secreted polypeptide molecules of the innate immune system and can remain bound to an antigen and to the surface of an APC at the same time. They can thus act as "bridges", and are thought, by virtue of this property, to promote internalization of antigens by APCs. The mode in which opsonins bind to antigens varies among opsonins, and can be covalent or noncovalent. In general, the antigen-binding moieties of innate opsonins differ from the antigen-binding moieties of immunoglobulins in that the former are relatively invariant among members of the same species, and do not undergo diversification during the ontogeny of an individual.

There have been a number of attempts to increase uptake of antigens by APCs by coupling an antigen via a non-peptide linkage to another molecule that can bind to the surface of an APC. Targeting moieties have included, for example, C3b (Jacquier-Sarlin et al., *Immunol* 84:164–70; Arvieux et al., *Immunol* 65:229–35), alpha-2 macroglobulin (Chu et al, *J Immunol* 152:1538–45; Chu and Pizzo, *J Immunol* 150:48–58), and molecules comprising idiotypes specific for immunoglobulin Fc receptors (Squire et al., *J Immunol* 152:4388–96; Gosselin et al., *J Immunol* 149:3477–81; Snider and Segal, *J Immunol* 143:59–65) or class II MHC molecules (Estrada et al., *Vaccine* 13:901–7; Berg et al., *Eur J Immunol* 24:1262–8; Carayanniotis and Barber, *Nature* 327:59–61).

Another approach to improving uptake of antigen by APCs has been to construct chimeric polypeptides comprising an antigen and an idiotypic portion of an antibody, in which the latter is specific for class II MHC molecules (Baier et al., *J Virol* 69:2357–65) or an immunoglobulin Fc receptor (Liu et al., *JCI* 98:2001–7).

Dempsey et al. (*Science* 271:348–50) constructed fusion proteins between C3d and an antigen, the fusion proteins being capable of binding to CR2-bearing cells such as B cells, reasoning that the B cell costimulation provided by C3d would increase the humoral immune response to the antigen. These fusion proteins do not bind to antigen presenting cells. Marked increases in antibody response were in fact observed, which were abrogated by in vivo antibody blockade of CR2.

SUMMARY OF THE INVENTION

The invention provides compositions and methods for modulating immune responses in subjects. The invention is based, at least in part, on the discovery that an in-frame translation fusion of an antigen with an APC binding domain of an opsonin forms a molecule, that is, a fusion polypeptide, which when administered to a subject modulates an immune response to the antigen.

Accordingly, the invention also pertains to recombinant nucleic acid molecules which include a nucleotide sequence encoding an antigen and a nucleotide sequence encoding an APC binding domain, and thus include a nucleotide sequence encoding a fusion polypeptide comprising the antigen and the APC binding domain.

As used herein, "modulation" means that a desired/selected response is more efficient, more rapid, greater in magnitude, and/or more easily induced than if the antigen had been used alone. The desired immune response can be stimulation/activation of a selected immune response, e.g., selective enhancement of an immune response to an antigen, or it can be inhibition of a selected immune response e.g., selective suppression, elimination, or attenuation of an immune response to an antigen, or a combination thereof.

As used herein, an "APC binding domain" refers to the whole of an innate opsonin or that portion or domain of an innate opsonin that binds to antigen presenting cells (APC binding domain).

In a fusion polypeptide according to the invention, different peptides or polypeptides are linked in-frame to each other to form a contiguous chimeric polypeptide. Thus, a first portion of the fusion polypeptide comprises an antigen and a second portion of the fusion polypeptide, either the amino- or carboxy-terminal to the first portion, comprises a function opsonin moiety. It is critical in the fusion polypeptide that the antigen retain its antigenicity and the APC binding domain retains its ability to facilitate or permit binding of the fusion polypeptide to the APC; that is, the two portions of the fusion polypeptide must be able to assume their natural structure to the extent that they retain the antigenicity and binding functions necessary to modulate the immune response according to the invention. The amino and carboxy-terminal orientation of the antigen and APC binding domain will most likely be determined by the location of the APC binding domain in the opsonin molecule; that is, if the APC binding domain is located near the amino terminus of the opsonin, then the amino-terminal portion of the opsonin may correspond to the amino terminus of the fusion polypeptide; similarly, if the APC binding domain is located near the carboxy terminus of the opsonin, then the amino-terminal portion of the opsonin may correspond to the carboxy terminus of the fusion polypeptide.

Examples of categories of antigens which can be encoded by the nucleic acid molecules include, for example, viral antigens, bacterial antigens, fungal antigens, protozoal and other parasitic antigens, tumor antigens, antigens involved in autoimmune disease, allergy and graft rejection, and other miscellaneous antigens.

APC binding domains of innate opsonins encoded by the nucleic acid molecules can include, for example, an APC binding domain of fibronectin, α2macroglobulin (a2m), C-reactive protein (CRP), complement component C1q, complement fragment C3b, complement component C4b, mannose binding protein, conglutinin, and surfactant proteins A and D.

The nucleic acid molecules of the invention can be used, for example, to modulate an immune response in a mammal to an antigen encoded by the nucleic acid molecule by direct administration of the nucleic acid.

Methods of the invention include the step of administering to an animal a nucleic acid molecule which encodes a fusion polypeptide comprising an antigen and a APC binding domain of an innate opsonin, or which encodes a polypeptide complex as defined herein, in an amount and over a period of time effective to modulate an immune response to the antigen in the mammal.

As used herein, an preferred "animal" is a non-rodent animal, preferably, a non-rodent mammal, more preferably, a primate, and most preferably, a human.

The invention also pertains to vectors which include the nucleic acid molecules of the invention, host cells which are transfected with such vectors, and transgenic animals which include the nucleic acid molecules of the invention.

In another embodiment of the invention, where a first and second portion of an opsonin, when covalently associated via a non-peptide bond, form an APC binding domain, them first or second portion of the opsonin may be fused in-frame to the antigen to form a fusion polypeptide. The remaining second or first portion, respectively, may then be covalently associated with the fusion polypeptide via a natural mechanism in the host cell and form a complex.

Therefore, in another aspect, the invention pertains to a multichain polypeptide complex comprising a first portion of an innate opsonin which in the presence of a second portion of an innate opsonin forms an APC binding domain, and a fusion polypeptide that comprises an antigen and the second portion of the opsonin. The first portion of the innate opsonin is associated with the fusion polypeptide containing the second portion of the opsonin via a covalent linkage. Therefore, the polypeptide complex comprises at least two polypeptide chains which, when covalently associated, form an APC binding domain. Furthermore, at least one of the chains may comprise an antigen.

Antigens and opsonins which can provide components of the fusion polypeptides are described herein.

In yet another aspect, the invention pertains to vaccine compositions. The vaccine compositions include nucleic acid molecules including nucleotide sequences encoding a fusion polypeptide or a polypeptide complex as described herein and a pharmaceutically acceptable carrier.

The vaccine compositions of the invention can be used for, for example, modulating in an animal an immune response to the antigen.

Methods of administering a vaccine according to the invention include the step of administering naked nucleic acid, which may be RNA or DNA, to the animal. As used herein, "naked" refers to nucleic acid which is substantially free from substances which facilitate entry of the nucleic acid into a host cell, for example, liposomes, ligands specific for cell surface receptors, endosomal disruption agents, etc.

DETAILED DESCRIPTION OF THE INVENTION

A composition of the invention comprises a fusion polypeptide which includes an antigen fused to a APC binding domain. The fusion polypeptide will bind to an APC with a binding constant having an affinity that is in the nanomolar range, and the antigen itself (i.e., free of the fusion polypeptide) will not bind to the same APC or will bind at a significantly lower affinity (at least 10-fold lower).

A composition of the invention also comprises a multichain polypeptide complex which includes (a) a first portion of an opsonin which when covalently associated with a second portion of the same opsonin forms an APC-binding domain and (b) a fusion polypeptide that includes an antigen and the second portion of the opsonin. That is, the fusion polypeptide will include an antigen and at least a portion of an opsonin that, when associated with an APC binding moiety of an innate opsonin, permits binding of the composition to an APC. As used herein, "associated with" refers to covalent bonding which is not peptide bonding, the covalent bonding being, for example, disulfide or hydroxyl bonding. The complex also will bind to an APC with a binding constant having an affinity that is in the nanomolar range, and the antigen itself (i.e., free of association with the APC-binding domain) will not bind to the same APC or will bind at a significantly lower affinity (at least 10-fold lower).

The compositions of the present invention are distinguished from prior art molecules compositions comprising non-peptide linkages between APC ligand and antigens in that the linkages of the invention can be produced using recombinant DNA techniques. Furthermore, this property allows an animal to be vaccinated with a nucleic acid encoding a fusion polypeptide of the invention, so that, when expressed as a secreted molecule in vivo, the fusion polypeptide is targeted to an APC, regardless of whether a non-APC, e.g. a rhabdomyocyte, expressed it. This is important since, for example, after intramuscular nucleic acid injection a significant amount of the nucleic acid is taken up by rhabdomyocytes, which are not generally considered to be APCs.

In addition, the compositions of the invention are distinguished from fusion polypeptides comprising antibody idiotypes by having an APC-binding portion that is a constituent of the innate immune system, i.e., that is substantially invariant among individuals of a species. Antibody idiotypes, in contrast, are generated and diversified in part by ontogenic processes such as VDJ recombination, junctional diversity, and somatic mutation. Thus, they vary substantially among individuals, and can be unique to individuals. Administration of both an allo-idiotype and another polypeptide, therefore, will often constitute coadministration of at least two foreign antigens. Coadministration of two foreign antigens can result in "antigenic competition" (Hunt et al., *Vaccine* 12:457–64; Rizvi et al., *Int J Exp Path* 71:761–70; Hammerl et al., *Mol Immunol* 25:313–20; Johansson et al., *PNAS* 84:6869–73; Babbitt et al., *PNAS* 83:4509–13), so that the immune response to a fusion polypeptide comprising two foreign antigens, one of which is an idiotype, might be substantially different from the immune response to a polypeptide comprising one foreign antigen and a non-foreign opsonin. In addition, the polypeptides of the invention, unlike immunoglobulins with idiotypes that bind to molecules on the surface of APCs, can bind to antigens that are not expressed on the cell surface.

Opsonins Useful According to the Invention

The term "opsonin" is used herein interchangeably with "innate opsonin". Both terms refer to a naturally occurring secreted polypeptide molecule which in nature may become bound to an antigen and also bound to the surface of an APC. Furthermore, in nature the opsonin can be bound contemporaneously to both the antigen and the APC to form a complex that facilitates uptake of the antigen by the APC.

Opsonins particularly useful in the invention are those which bind APCs of monocytic lineage. Monocyte-lineage APCs include, for example, monocytes, macrophages, and dendritic cells.

One particularly useful opsonin is a biologically active fragment of C3 and the APCs are uncultivated peripheral blood monocytes.

If the molecule comprises a fragment of C3, the APC binding domain must bind to CR1 with a greater affinity than it binds to CR2. This definition of a fragment of C3 therefore excludes C3d and C3bi.

An innate opsonin can bind to an antigen other than a molecule that is physiologically expressed on the surface of an APC.

According to the invention, innate opsonins are present in most individuals of a given species, and are structurally invariant among most members of a species, except that allelic variations may exist. During the ontogeny of most individuals, a gene encoding an innate opsonin does not undergo mutation or rearrangement in most of the cells that express the opsonin.

An opsonin can also be a polypeptide molecule, e.g., C3, which can be proteolytically processed such that at least one product of the processing step or steps can be bound stably and contemporaneously to an antigen, via a physiologically occurring linkage, and to the surface of an APC.

Other particularly useful opsonins bind to receptors on monocyte-lineage APCs such as receptors which play a role in innate immunity. Examples of such receptors include CR1, CR3, the C1q receptors and receptors containing a component of the C1q receptors. Examples of opsonins which can be used in the compositions and methods of the invention include fibronectin (e.g., Genbank accessions X02761, K00799, K02273, X82402, X00307, X00739), CRP (e.g., Genbank accessions X17496, M111880, M11881, M11882), complement components such as C1q (e.g., Genbank accessions X66295, M22531, X03084, X58861, and Swiss-Prot accessions P02747, P02745), complement fragments such as C3b (e.g., Genbank accessions K02782, K02765), mannose binding protein (e.g., Genbank accessions S42292, S42294, X15422), conglutinin (e.g., Genbank accession X71774), alpha-2-macroglobulin (e.g., Genbank accessions M93264, M11313), and surfactant proteins A (e.g., Genbank accessions M68519, S48768) and D (e.g., Genbank accessions L40156, X65018, S38981), and their homologues among species.

There are a number of examples of opsonin fragments that comprise APC binding moieties. For example, Las Holtet et al., 1994, *FEBS Lett* 344:242 describe a carboxy-terminal fragment of human a2m (val1299-ala1451) that binds with high affinity to the a2m receptor. Fragments comprising amino acids 1314–1451 of human a2m and the corresponding domain of rat a2m also bind to a2m receptors, albeit with 1–2% of the affinities of native a2m (Van Leuven et al., 1986, *J Biol Chem* 261:11369; Enghild et al., 1989, *Biochemistry* 28:1406; Salvesen et al., 1992, *FEBS Lett* 313:198; Sottrup-Jensen et al., 1986, *FEBS Lett* 205:20).

Becherer and Lambris, 1988, *J Biol Chem* 263:14586 describe fragments of C3b that bind to CR1, e.g., C3c, fragments of C3 generated by elastase treatment and comprising the N-terminal of the alpha' chain of C3b, and a synthetic peptide comprising the 42 N-terminal amino acids of the C3b alpha' chain. A binding sequence in C3 for CR3 has also been described (Wright et al., 1987, *PNAS* 84:4235).

"Collagen stalks" of C1q, which are N-terminal fragments obtained by pepsin digestion, bind to the C1q receptor (Reid, 1981, *Methods Enzymol* 80:16; Malhotra et al., 1993, *Biochem J* 293:15). Malhotra et al., ibid., also provide evidence that an APC binding moiety of conglutinin is comprised by its 55 N-terminal amino acids. Ezekowitz (U.S. Pat. No. 5,270,199) offers a putative APC binding site in human mannose binding protein consisting of nucleotides 370–438 of FIG. 2 in the '199 Patent.

Families of Opsonins Useful According to the Invention

Some sets of opsonins can be regarded as structurally and functionally similar. For example, one family comprises fragments of complement components C3 and C4. These two components are highly structurally homologous, and each possesses an intramolecular thiolester bond that is broken when a peptide (C3a or C4a respectively) is proteolytically cleaved from the native molecule. Disruption of the thiolester makes available a chemical structure that can form an ester linkage with an antigen. The moiety of C3 on which this ester bond resides, i.e. the non-C3a moiety, is designated C3b, and C4b is the analogous product of C4 cleavage. C3b can be further proteolysed by proteins such as factor I to yield fragments such as C3bi and C3d, which also remain linked to the antigen via the ester bond.

However, not all biologically active fragments of C3 are opsonins according to the invention. For example, C3 does not bind to surface receptors on peripheral blood monocytes (refs). Its primary biological activity is thought to be to provide costimulatory transmembrane signals directly to B lymphocytes through CR2. Furthermore, such an approach is limited to increasing a humoral immune response, whereas targeting antigens to monocytes can modulate either humoral or cellular immune responses, since APCs of monocytic lineage influence both types of response through their interactions with "helper" T cells.

There are four structurally unique proteins that are known to function as high affinity receptors for biologically active, membrane-bound fragments of C3 and/or C4. CR1 is the major receptor for the C3b fragment of C3 and C4b fragment of C4. It is expressed on monocytes and monocyte-derived APCs, among other cell types. CR2 is the major receptor for the fragment of C3 known as C3d, and is expressed on, e.g., mature B lymphocytes, but not on cells of monocytic lineage. The major role of CR2 on B lymphocytes is believed to be direct costimulation of B cells in concert with their cognate antigens.

CR3 is expressed primarily by neutrophils and monocytes and is also expressed on FDC, Kupffer cells, and NK cells. CR3 is a C3 fragment receptor with a primary specificity for C3 bi. CR3 has been proposed as an important organizer of cytoskeletal events necessary for adhesive interactions and membrane reorganization during processes such as phagocytosis.

CR4 is a member of the beta2 integrin family, and its alpha chain is structurally similar to the alpha chain of CR3 and LFA-1. Its primary physiologic ligand is believed to be C3d,g; however, its biologic activities are less well understood than CR3.

Another example of a family of innate opsonins is the collecting, a group of collagenous C-type lectins that comprises complement component C1q, mannose binding protein, surfactant proteins A and D, and conglutinin. Each molecule comprises a lectin domain that can bind to an antigen, and a collagenous domain that can bind to receptors on phagocytic mononuclear cells, including receptors that are wholly or partially identical to the C1q receptor (Tenner et al., *Immunity* 3:485–93; Guan et al., *J Immunol* 152:4005–16; Geertsma et al., *Am J Physiol* 267:L578–84; Miyamura et al., *Biochem J* 300:237–42; Malhotra et al., *J*

*Exp Med* 172:955–9; Malhotra et al., *Biochem J* 293:15–19). Most known collectins comprise multiple polypeptide chains, in some cases homomeric and in others heteromeric, that are assembled post-translationally, in part by covalent cross-linkage of hydroxyproline and hydroxylysine residues. Collectins are demonstrated to be opsonins in, for example, Pikaar et al., *J Infect Dis* 172:481–9; Alvarez-Dominguez et al., *Infection & Immunity* 61:3664–72; O'Riordan et al., *J Clin Invest* 95:2699–710; Kuhlman et al., *J Exp Med* 169:1733–45; and Geertsma et al., op cit.

Among the other innate opsonins useful according to the invention are C-reactive protein (CRP), alpha-2 macroglobulin (a2m), and fibronectin. CRP, a member of the pentraxin family of molecules, binds to receptors on cells of monocytic lineage and has been shown to be an opsonin (Culley et al., *J Immunol*, 1995, 156;4691). Alpha-2 macroglobulin, like C3 and C4, comprises an internal thiolester bond that can be disrupted when the molecule is proteolysed. Such disruption allows covalent binding of the molecule to an antigen, and binding of alpha-2 macroglobulin to an APC can promote uptake of the conjugate (Straight et al., *Biochemistry* 27:2885–90). Fibronectin binds to the alpha 5 beta 1 integrin and can also bind to various antigens, allowing it to function as an opsonin (Cosio, *J Lab Clin Med* 103:613–9; Czop and Austen, *J Immunol* 129:2678–81).

Fusion polypeptides have previously been constructed between portions of opsonins and relatively limited group of other polypeptides for purposes such as to facilitate isolation and purification of the opsonin or to elucidate structure-function relationships. For example, a portion of alpha-2 macroglobulin has been fused to carbonic anhydrase II to facilitate expression of the a2m moiety in a bacterium (Mottaqui-Tabar et al., *Ann N.Y. Acad Sci* 737 493–5). Short portions of C3 from non-human species have been fused with human C3 to elucidate structure-function relationships (Lambris et al., *J Immunol* 156:4821–32). A heptapeptide recognition site for Tobacco Etch Virus protease was introduced into alpha-2 macroglobulin to investigate the function of the a2m bait region (Van Rompaey et al., *Biochem J* 312:191–5). Carbohydrate recognition domains of opsonins or adhesion molecules have been fused to portions of opsonins in order to demonstrate transfer of ligand specificity (Blanck et al., *J Biol Chem* 271:7289–92; Ogasawara et al., *J Biol Chem* 269:29785–92). Peptides comprising the Arg-Gly-Asp (RGD) APC-binding moiety of fibronectin have been fused to a number of polypeptides in order to study, e.g., structure-function relationships and amphibian cell biology (Alfandari et al., *Mech Dev* 56:83–92; Ramos et al., *J Cell Biol* 134:227–40; Ebeling et al., *Eur J Immunol* 26:2508–16). The invention, in contrast, provides compositions that are useful for preventing or treating disease.

Opsonins are thought to act as a link or coupling agent between the antigen and the APC to allow more efficient binding, engulfment, and internalization of the antigen. A molecule is defined herein as an opsonin useful in the invention if it binds to a cognate antigen as determined in one or more of the assays of opsonicity described herein. According to the invention, opsonicity is determined in part by detection of binding to an APC and an antigen. For example, fragments of C3 can be bound to sheep red blood cells (SBRC); and opsonins with lectin activity can be directly admixed with microorganisms bearing a cognate carbohydrate.

According to the invention, an "APC binding domain" is a portion of an opsonin which permits binding of a fusion polypeptide containing that domain and an antigen to an APIC. A fusion polypeptide or a complex of the invention comprises an APC binding domain if it can bind to a naturally occurring APC surface molecule with an affinity at least in the nanomolar range and if binding to said molecules does not occur via the antigen. Binding via the antigen is easily discernible by testing free antigen for affinity to said surface molecule. Binding via antigen does not occur if the affinity of free antigen is at least 10-fold lower than that of the polypeptide or complex.

A "fusion polypeptide complex" contains first and second portions of an opsonin that together form an APC binding domain and together permit binding of a fusion polypeptide containing one such portion fused in-frame to an antigen to bind to an APC. A first or second portion of an APC binding domain does not correspond to an APC binding domain in itself, but forms an APC binding domain only when covalently associated with the second or first portion, respectively. This complex can be produced when the gene encoding the fusion polypeptide is expressed in a cell and coexpressed with a gene encoding a chain of an opsonin that contains the other portion (first or second portion) of the APC binding domain.

An APC binding domain will also, of course, includes a complete opsonin polypeptide, e.g., C3.

It is particularly preferred according to the invention where the APC binding domain consists essentially of an APC-binding moiety of an innate opsonin.

A fusion polypeptide according to the invention comprises an "APC binding domain of an opsonin" if the fusion polypeptide can bind to a receptor that is physiologically expressed on an APC with an affinity at least in the nanomolar range. Fusion polypeptides according to the invention do not include chimeric proteins consisting only of a first opsonin or APC binding domain thereof fused to a second different opsonin, or APC binding domain thereof, but may include one or more opsonins or Apc binding domains thereof fused to an antigen.

A fusion polypeptide or multichain complex of the invention will bind to the antigen presenting cell via the opsonin portion of the molecule rather than via the antigen. This is easily distinguishable as free antigen will not compete with a fusion polypeptide for APC binding if the polypeptide or complex binds to the APC via the APC binding domain, whereas free antigen will compete with the fusion polypeptide binding to the APC if the polypeptide or complex binds to the APC via the antigen portion of the polypeptide or complex. Therefore, a fusion polypeptide of the invention comprises an APC binding domain of an opsonin if this APC binding domain can bind to a receptor that is physiologically expressed on an APC with an affinity at least in the nanomolar range when included in a fusion polypeptide that does not comprise a second portion, heterologous to the first opsonin, which, in isolation, can bind to a receptor that is physiologically expressed on an APC with an affinity at least in the nanomolar range. APC-binding domains that do not comprise entire opsonins have been described, for example, for mannose binding protein (Tenner et al., *Immunity* 3:485–95), C3b (Becherer and Lambris, *J Biol Chem* 263:145891), conglutinin (Malhotra et al., *Biochem J* 293:15–19), and fibronectin (Czop and Austen, *J Immunol* 129:2678–81).

In another preferred embodiment, the APC binding moiety does not require the amino acid sequence RGD in order to bind to an APC receptor.

Assays for Determining Opsonicity According to the Invention

Assay 1

In one assay of opsonicity, as described by O'Rear and Ross in Current Protocols in *Immunology*, 1994, John Wiley & Sons, pp. 13.4.5–9, SRBC bound via a physiologically occurring linkage to the candidate opsonin molecule are obtained. APCs from the species to which the candidate opsonin is native are suspended at $4 \times 10^6$/ml in ice-cold HBSS with 1% (w/v) Cohn fraction of BSA. If the candidate opsonin is a fragment of C3, the APCs are freshly drawn, uncultivated peripheral blood monocytes. SRBC linked to the candidate opsonin or control SRBC (identical to the former but not linked to the candidate opsonin) are suspended in the same solution at $2 \times 10^8$/ml. 100 ul of SRBC suspension and 100 ul of APC suspension are mixed in a $10 \times 75$ mm plastic tube. The tube is rotated at 40 rpm at 37° C. for 2–20 min. A small drop of the suspension is placed on a slide, covered with a coverslip, and allowed to stand for 5–10 min. Excess fluid can be removed by pressure on the coverslip, and the coverslip can be sealed to the slide, e.g. with clear nail polish. The slide is examined microscopically, and the percentage of APCs visibly adherent to 4 or more SRBCs is determined. If said percentage is 50% or greater when there are up to $4 \times 10^4$ candidate opsonin molecules/SRBC', the candidate opsonin can be an opsonin.

Assay 2 (For protease-activated candidate opsonin)

Candidate opsonin or radiolabeled Candidate opsonin is treated with a 1.5–3 fold molar excess of protease (0.05 M triethanolamine-0.1 M NaCl, pH 8.0, room temperature overnight). In this assay, the protease can serve as the antigen or an excess of another antigen can be added. Prior to binding studies, the candidate opsonin-antigen complex is dialyzed against HBSS (4° C.).

Candidate opsonin-antigen complex binding to monocytes is measured by incubating labeled ligand at a concentration up to 1.0 M with $(1.5-4.0) \times 10^6$ monocytes in 200 $\mu$l volume on ice. Nonspecific binding of radiolabeled ligands is determined in the presence of a 100-fold molar excess labeled candidate opsonin-antigen complex. The unbound ligand is separated from the cells and cell-bound ligand by rapid vacuum filtration on glass fiber filters. Studies are performed on ice to avoid potential complications due to endocytosis. Binding constarts and the number of sites per cell are determined by analysis and by nonlinear curve fit. If candidate opsonin-antigen complex affinity for a monocyte binding site is in at least the nanomolar range, the candidate opsonin is an opsonin.

Assay 3

Part I

To directly evaluate whether candidate opsonin is bound to the surface of *P. carinii*, immunoelectron microscopy is performed. *P. carinii* are isolated from bronchoaveolar lavage (BAL) of moribund infected rats using TBS with 1 mM calcium to preserve surface-bound candidate opsonin. Isolated organisms are fixed in periodate-lysine-paraformaldehyde buffer and embedded in Lowacryl mounting medium (Ted Pella, Inc., Redding, Calif.). Ultrathin sections are obtained, blocked with normal goat serum (2%) for 1 h, and incubated with either rabbit anti-candidate opsonin or nonimmune rabbit IgG (25 $\mu$g/ml) overnight. After washing, the sections are subsequently incubated with goat and rabbit IgG conjugated to 15 nM colloidal gold (Amersham Corp., Arlington Heights, Ill.). The sections are washed again and examined on a transmission electron microscope (model 6400:JEOL USA, Inc., Peabody, Mass.).

Part II

The attachment of *P. carinii* to cultured alveolar macrophages in the presence or absence of antibody to SP-D or with the addition of purified SP-D is quantified as follows. Adherence of *P. carinii* to alveolar macrophages is assayed by $^{51}$Cr-labeling the organisms. *P. carinii* are isolated from infected rats with TBS containing 1 mM calcium to prevent loss of surface-bound candidate opsonin. The organisms are radiolabeled by incubation for 8 h at 37° C. in 2 ml of DME containing 20% FCS and 200 $\mu$Ci of $^{51}$Cr-sodium chromate (New England Nuclear). Normal alveolar macrophages are lavaged from healthy rats and plated in tissue culture plates ($1 \times 10^5$) cells/well) which are been precoated with normal rat IgG (100 $\mu$g/ml$\times$60 min) in order to ensure firm adherence of the macrophages. After 1 h, the macrophages are gently washed with HBSS to remove nonadherent cells. >95% of macrophages are adherent after this wash. $^{51}$Cr-*P. carinii* ($1 \times 10^6$) containing surface-associated candidate opsonin are added to the macrophages and incubated at 37° C. for an additional hour. Subsequently, nonadherent *P. carinii* are removed by washing. The macrophage monolayers containing adherent *P. carinii* are solubilized in 1 N NaOH and quantified. Adherence of *P. carinii* is defined as: percentage of adherence=(A/A+B)$\times$100, where A=$^{51}$Cr-*P. carinii* associated with the monolayer, and B=unattached $^{51}$Cr-*P. carinii*. To assess the effect of candidate opsonin on the attachment of *P. carinii* to alveolar macrophage lung cells in culture, *P. carinii* adherence assays are conducted in the presence or absence of a polyclonal rabbit antibody generated against the candidate opsonin (100 $\mu$g/ml).

If candidate opsonin binding to *P. carinii* is apparent in Part I and if, in Part II, % adherence is diminished in the presence of anti-candidate opsonin with statistical significance of $P<0.05$, the candidate opsonin is an opsonin.

Assay 4

Association of bacteria with adherent monocytes is measured as follows. Endotoxin level in the modified PBS and in all buffers used is below 50 pg/ml as determined by the Limulus assay. $5 \times 10^3$ monocytes in modified PBS are allowed to adhere to the wells of a Terasaki plate for 2 h at 37° C. After nonadherent cells are removed by three washes with PBS, $5 \times 10^4$ FITC-labeled bacteria in 0.5 ml buffer with or without 10–50 micrograms/ml of candidate opsonin are added. A bacteria-to-monocyte ratio of 10:1 to 50:1 is used. After 30 min of incubation at 37° C. in the dark, the nonadherent bacteria are removed by five washes with warm PBS. Assays are performed in quadruplicate; in each well, the number of bacteria associated with $\geq 100$ monocytes is counted under a flourescence microscope using$\times$400 magnification. Results are expressed as the number of bacteria associated with 100 monocytes. If this number with candidate opsonin can be at least twice that without candidate opsonin, the candidate opsonin is an opsonin.

Assay 5

Part I

About $1 \times 10^7$ to $6 \times 10^7$ bacteria per ml are incubated (20 min, 0° C.) with 10 mcg/mi of $^{125}$I-candidate opsonin in a total volume of 0.7 ml. of PBS aliquots, 100 $\mu$l, of the reaction mixtures are layered over 150 $\mu$l of an oil cushion (60% dibutyl phthalate, 40% dioctyl phthalate [Eastman Kodak Co., Rochester, N.Y.]), and the mixtures are centrifuged (10,000$\times$g, 60 s, 4° C.). The tip of the tube, containing the cell pellet, is cut with a Mozart razor blade, and the radioactivity is counted.

Part II

APCs are plated in 96-well tissue culture plates (Costar, Cambridge, Mass.) at $2 \times 10^5$ cells per ml the evening before use. $2\times10^6$ bacteria per well (0.1 ml per well) are added to the culture plates with or without 100 mcg/ml of candidate opsonin. The plates are then centrifuged at 1,000×g for 7 min. After 15 min at 37° C. to allow the uptake of bacteria, free bacteria are removed by several washes with cold PBS. They are then incubated (45 min, 37° C.) in RPMI 1640 plus an amount of antibiotic that, when present in the culture for 45 min, kills all extracellular bacteria. The end of this incubation period is considered time zero. Monolayers are washed three times with Hanks' balanced saline solution, and the same volume of RPMI 1640 (R0) is added. The cells are lysed by using several cycles of freezing and thawing. The number (CFU) of viable bacteria per well is determined by quantitative plate counts on blood agar plates (Columbia blood agar; Becton Dickinson, San Jose, Calif.) after 24 h of incubation. Each result is given as the mean of three determinations.

If, in Part I, candidate opsonin-treated bacterial pellet has >75 KCPM and this incorporation can be inhibited by unlabeled candidate opsonin, and if in Part II the CFU with candidate opsonin is greater than without (P<0.05), the candidate opsonin can be an opsonin.

Assay 6

200 μl of GHBSS (Hanks Balanced Salt Solution) +0.1% of gelatin containing 10 m mol $CaCl_2$) containing $10^7$ bacteria is prepared. The bacteria are then incubated at 4° C. with 20–100 μg/ml of candidate opsonin. Binding assays are done in the presence or absence of a competitive inhibitor. After incubation for 30 minutes, the bacteria are washed five times in a GHBSS+10 mmol $CaCl_2$ at room temperature in a microfuge at 1,300 g for 3 minutes. Thereafter, a 1:1,000 dilution of rabbit anti-candidate opsonin antiserum is incubated with the bacteria for 1 h in PBS+5% FCS and 10 mmol $CaCl_2$ and then the bacteria are washed three times in GHBSS+10 mmol $CaCl_2$ plus 0.05% Tween 20. Binding of anti-serum to bacteria is detected by a 1:1,000 dilution of goat anti-rabbit IgG conjugated to rhodamine (Fisher Pharmaceuticals, Orangeburg, N.Y.). After incubation, the bacteria are washed five times in GHBSS+10 mmol $CaCl_2$ plus 0.05% Tween 20, smeared onto glass slides and allowed to air dry. Thereafter bacteria are fixed with 100% ice cold methanol for 5 minutes. Negative controls included the absence of candidate opsonin and no first step antibody. Numerous fields of triplicate assays are examined by fluorescence microscopy.

Part II Association of Radiolabeled Bacteria with Cells.

$10^7$ radiolabeled bacteria are resuspended in 200 μl of GHBSS+10 mmol $CaCl_2$ and are incubated with or without candidate opsonin ranging from 2 μg/ml to 40 μg/ml at 4° C. for 30 min. The bacteria are then washed three times in GHBSS+10 mmol $CaCl_2$ for 3 min at room temperature in a microfuge at 1,300 g, resuspended in 50 μl of GHBSS and added to a 1-ml suspension containing on the order of $10^6$ APCs (GHBSS). The bacteria and APCs are gently rocked at 37° C. for 20 min and thereafter the unattached bacteria are removed by five washes using differential centrifugation at 82 g in a microfuge. Before the last wash, an aliquot from each sample is plated on a Labtek slide and cells are adhered for 10 min, fixed in methanol, stained with Geimsa, and scored by light microscopy. To score the cells plated on the Labtek slides, at least 400 cells are counted. The phagocytic index represented the number of attached or ingested particles per 100 PMNs. The pellet from above containing cells and radiolabeled bacteria is then lysed in 100 μl PBS+0.5% Triton X-100 and the radioactivity is measured in a scintillation counter. If, in Part I, specific binding of candidate opsonin to bacteria is evident, and in Part II the specific uptake of bacteria, in cpm, is more than three times greater with candidate opsonin than without, the candidate opsonin can be an opsonin.

Assay 7

Part I

To investigate binding to *L donovani* promastigotes cultures are seeded at $5\times10^5$ parasites $ml^{-1}$. At regular time points up to 9 days, a fraction of parasites are counted, washed, and resuspended in 1% BSA, 0.5 mM $Ca^{2+}$. 0.05% $NaN_3$, Tris-buffered saline (TBS), (10 mM Tris-HCl, 0.15 M NaCl, pH 8.0) (diluent) to $2\times10^5$ $ml^{-1}$. Fifty microliters of this suspension are then added to 200-μl microfuge tubes containing 70 μl 5 μg/mil radiolabled C-reactive protein (CRP) (0.12 μCi/μg) in diluent without EDTA, which had been layered over 150 μl of a dinonyl phthalate/dibutyl phthalate (40:60 v/v) oil mixture. Parasites are incubated for 1 h and centrifuged through the oil layer, the cell pellet Is cut off, and associated CRP is detected by gamma counting. Each assay is performed in triplicate. The concentration dependency of CRP, binding to promastigotes is also measured as above, using an activity of 0.045 μCi/μg and a twofold dilution series from 60 to 0.015 μg/ml CRP.

Part II

APCs are plated out at $1\times10^6$ cells/well on glass coverslips in a 24-well tissue culture plate. Cells are incubated in RPMI 1640 (Life Technologies) supplemented with 10% PCS, 1 mM glutamine, 200 U/ml penicillin and 200 μg/ml streptomycin in a humidified incubator at 37° C. After 24 h, nonadherent cells are removed and remaining cells are used after 6 days. Promastigotes are incubated with or without CRP at 30 μg/ml in RPMI 1640 for 1 h and then washed three times before adding to the APC cultures at $10^6$/well. Promastigotes are allowed to infect APCs for 1 h, then cells are washed, fixed with methanol, and Geimsa stained (BDH, Poole, Dorset, U.K.) before counting. The percentage of APCs infected and the number of parasites/100 macrophages is determined from quadruplicate cultures.

If in Part I the affinity of candidate opsonin for parasites is at least in the nanomolar range and in Part II the number of parasites taken up/100 APCs is, with candidate opsonin, at least twice that without candidate opsonin, the candidate opsonin can be an opsonin.

Assay 8

Part I

Portions (0.5 ml) of [$^{35}$S]methionine-labeled culture medium containing 5 percent fetal calf serum and the candidate opsonin are incubated for 30 minutes at room temperature with 0.1 ml or 0.2 ml of a 10 percent suspension of a microorganism). The microorganisms tested may include, for example, *Salmonella typhimurium, Bacillus subtilis, Staphylococcus aureus, Escherichia coli,* and *Saccharomyces cerevisiae.* Bound proteins are released by boiling in buffer containing 2 percent SDS and 0.1 M dithiothreitol and are analyzed on a 5 percent SDS gel.

Part II

Fixed bacteria (0.1 ml; 10 percent by volume; $10^{10}$ organisms per millileter), labeled with [$^3$H]thymidine, are incubated with 0.1 ml of serum with or without depletion of the candidate opsonin. After being washed with PBS, the bacteria are incubated with on the order of $1\times10^7$ APCs in a final volume of 0.9 ml PBS containing divalent cations. At intervals 0.2 ml is removed to ice-cold PBS with N-ethyimaleimide (2 mM) to block further endocytosis, and the cells are washed (at about 100 g for 10 seconds).

If in Part I a band corresponding to the candidate opsonin is apparent, and if in Part II the CPM after 6–10 min of incubation is at least three times greater for undepleted samples with serum than with depleted serum, the candidate opsonin can be an opsonin.

In lieu of results form Parts I of assays 3, 5, 6, 7, 8, a candidate opsonin that satisfies Part II of an assay can be an opsonin if it can bind to the antigen of the assay with an affinity in at least the nanomolar range.

Linkage of Antigen to Opsonin

An antigen is linked to an opsonin according to the invention via recombinant DNA techniques to form a chimeric gene, and expression of the chimeric gene in a host cell. Therefore, the linkage contemplated in the invention is limited to a peptide linkage for formation of an in-frame fusion polypeptide.

A flexible linker sequence may be inserted into the fusion polypeptide between the antigen and the opsonin. For example, a polygylcine/polyserine-containing sequence such as $(Gly_4Ser)_2$. See Huston et al., 1991, *Meth. Enzymol.* 203:46.

Production of Fusion Polypeptide and Fusion Polypeptide Complexes

A fusion polypeptide according to the invention is produced in vivo or in vitro in a host cell by expression of the gene encoding the fusion polypeptide or by coexpression of the gene encoding the fusion polypeptide and a gene encoding a polypeptide chain which when associated with the fusion polypeptide to form a complex, permits binding of the complex to the APC. When two such genes are coexpressed, the fusion polypeptide and the polypeptide chain naturally form an association in the cell, for example, by disulfide bonding or by cross-linking between hydroxylated amino acids, such as via a lysine or proline residue.

Nucleic Acid Sequences

Another aspect of the invention features isolated nucleic acid molecules which include a nucleotide sequence encoding an antigen fused in one reading frame to a nucleotide sequence encoding an APC binding domain of an innate opsonin. The nucleic acid molecule also may include a sequence encoding a first or second portion of an opsonin, which portions correspond to fragments of an opsonin that form an APC binding domain. Where the nucleic acid sequence encodes a polypeptide complex according to the invention, the sequence encoding the fusion polypeptide and the sequence encoding the chain which in association with the fusion polypeptide forms an APC binding domain may be coexpressed and therefore under coordinated or the same gene control elements.

The phrase "nucleic acid molecule" as used herein is intended to include such fragments and refers to DNA molecules (e.g., cDNA or genomic DNA) and RNA molecules (e.g., mRNA). The nucleic acid molecule can be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be free of other cellular material. The term "fragment" as used herein refers to a portion of a nucleic acid molecule or polypeptide or other molecule described herein.

Typically, the nucleotide sequence encoding the antigen and the nucleotide sequence encoding the APC binding domain can be fused to form a "fusion gene" according to techniques known in the art. For example, in one embodiment, attachment/linkage of nucleic acid fragments coding for different polypeptide sequences can be performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be performed using anchor primers which give rise to complementary overhangs between two consecutive gene fragments which can subsequently be annealed to generate a chimeric gene sequence (see, e.g., *Current Protocols in Molecular Biology,* eds. Ausubel et al. John Wiley & Sons: 1992).

Antigens Useful According to the Invention

The term "antigen" as used herein refers to a molecule which can initiate a humoral and/or cellular immune response in a recipient of the antigen. The antigen is preferably an agent that causes a disease for which a vaccination would be advantageous treatment. The antigen portion of the fusion polypeptide is preferably at least 8 amino acids, and is preferably no longer than 25 amino acids, and preferably does not include more than 10 contiguous amino acids of an opsonin, or a lectin binding domain of a eukaryotic intercellular adhesion molecule, or a reporter molecule such as β-galactosidase. As used herein, a "lectin binding domain" refers to a carboxy-terminal carbohydrate recognition domain of a protein, for example exon 4, nucleotides 439–813 of human mannose binding protein. "Complement-fixing domain" refers to a collagen-like segment having a repeated pattern of Gly-X-Y (where X and Y represent any amino acid) similar to those of non-fibriallar collagen genes. The structure is consistent with those of an effector region which interacts with complement components; for example, exon 2, nucleotides 253–369 of human mannose binding protein.

Antigens can be any type of biologic molecule including, for example, simple intermediary metabolites, sugars, lipids, and hormones as well as macromolecules such as complex carbohydrates, phospholipids, nucleic acids and proteins. According to the invention, cells that comprise or are attached to a molecule that can elicit an immune response are also considered antigens. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1–NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; Mycobacterium tuberculosis bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Fungal antigens which can be used in the compositions and methods of the invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, plasmodium falciparum antigens such as merozoite surface antigens, sporozoite surface antigeuns, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75–77 kDa antigen, the 56 kDa antigen and other trypanosomal antigen components.

Tumor antigens which can be used in the compositions and methods of the invention include, but are not limited to, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the invention that antigens from any type of tumor cell can be used in the compositions and methods described herein.

Antigens involved in autoimmune diseases, allergy, and graft rejection can be used in the compositions and methods of the invention. For example, an antigen involved in any one or more of the following autoimmune diseases or disorders can be used in the present invention: diabetes mellitus, arthritis (including rheumatoid arthritis, juvenile rheumatoid arhritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

Examples of miscellaneous antigens which can be can be used in the compositions and methods of the invention include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

In one embodiment, the antigen comprises an antigen of a bacterium that infects animals. In a preferred embodiment, the antigen comprises an antigen of a virus, fungus, parasite, chlamydia, or rickettsia that infects animals. In another preferred embodiment, the antigen is a target of a pathologic autoimmune response. In yet another embodiment, the antigen comprises greater than seven amino acids. In a further embodiment, the antigen is a short peptide comprising no more than twenty amino acids, or preferably no more than twenty-five. It is preferred that the antigen comprise neither more than ten contiguous amino acids of an opsonin, nor a lectin domain of an adhesion molecule, nor a reporter protein such as a portion of beta galactosidase. If the opsonin moiety is derived from a2m, it is preferred that the antigen is neither carbonic anhydrase nor a heptapeptide comprising a cleavage site for the Tobacco Etch Virus protease. If the opsonin moiety is derived from mannose binding protein, it is preferred that the antigen is neither CD4 nor a toxic portion of a cytotoxin.

Vectors According to the Invention

Yet another aspect of the invention pertains to vectors, preferably expression vectors, containing nucleic acid molecules of the invention (or a portion or fragment thereof. As used herein, the term "vector" refers to a nucleic acid molecule capable of transporting another nucleic acid to which it has been linked. One type of vector is a "plasmid", which refers to a circular double stranded nucleic acid loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant nucleic acid techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that tie recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion polypeptides or peptides, encoded by nucleic acids as described herein.

The recombinant expression vectors of the invention can be designed for expression of the nucleic acid molecules of the invention in prokaryotic or eukaryotic cells. For example, the polypeptides encoded by the nucleic acid molecules of the invention can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992)

*Nuc. Acids Res.* 20:2111–2118). Such alteration of nucleic acid sequences of the invention can be carried out by standard nucleic acid synthesis techniques.

In another embodiment, the expression vector is a yeast expression vector. Examples of vectors for expression in yeast *S. cerivisae* include pYepSec1 (Baldari. et al., (1987) *Embo J* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, the polypeptides encoded by the nucleic acid molecules of the invention can be expressed in insect cells using baculovirus expression vectors. Baculovirus vectors available for expression of proteins in cultured insect cells (e.g., Sf9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, the polypeptides encoded by the nucleic acid molecules of the invention are expressed in mammalian cells using a mammalian expression vector. Examples of mammalian expression vectors include pCDM8 (Seed, B., (1987) *Nature* 329:840) and pMT2PC (Kaufman et al. (1987), *EMBO J:* 6:187–195). When used in mammalian cells, tie expression vector's control functions are often provided by viral regulatory elements. For example, commonly used promoters are derived from polyoma, adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byme and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the -fetoprotein promoter (Campes and Tilghman (1989) *Genes Dev.* 3:537–546).

In one embodiment, a recombinant expression vector containing a nucleic acid molecule encoding a fusion polypeptide of the invention is produced. The fusion polypeptides of the invention, i.e., fusion polypeptides which include an antigen portion and a functional opsonin moiety, can be produced by recombinant expression of a first nucleotide sequence encoding an antigen and a second nucleotide sequence encoding a functional opsonin moiety as described, far example, in U.S. Pat. No. 5,116,964 to Capon et al., the entire contents of which are hereby incorporated by reference. Fusion polypeptides, which include or do not include a linker amino acid sequence or an amino acid sequence directing secretion of the polypeptide which is not native to either the antigen or the opsonin amino acid sequences, produced by recombinant techniques can be secreted and isolated from a mixture of cells and medium containing the protein or peptide. Alternatively, the fusion polypeptide can be retained cytoplasmically and the cells harvested, lysed and the protein isolated. A cell culture typically includes host cells, media and other byproducts. Suitable media for cell culture are well known in the art. Polypeptides and peptides can be isolated from cell culture medium, host cells, or both using techniques known in the art for purifying proteins and peptides. Techniques for transfecting host cells are described in further detail herein.

For example, fusion polypeptides including one or more peptide or polypeptide antigens and one or more functional opsonin moieties can be produced by constructing a fusion gene which includes a nucleotide sequence encoding one or more antigens and a nucleotide sequence encoding one or more functional opsonin moieties. The fusion polypeptide product of the fusion can be expressed and then administered to a recipient mammal, subject etc. as described herein. Libraries of such fusion genes can be generated from microbes, tumor cells, allografts, xenografts, or other gene-containing entities by cloning the entire set of genomic or expressed nucleic acids or any subset thereof into an expression vector which contains one or more nucleotide sequences encoding one or more functional opsonin moieties such that a multitude of fusion genes including one or more opsonins are produced. These fusion genes can also be administered as described herein.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, a polypeptides encoded by nucleic acid molecules of the invention can be expressed in bacterial cells such as *E. coli*, insect cells, yeast or mammalian cells (such as Chinese hamster ovary cells (CHO) or COS cells). Other suitable host cells are known to those skilled in the art.

Preparation of Host Cells Containing Nucleic Acid Molecules of the Invention via In Vitro and Ex Vivo Methods Vector nucleic acid can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual,* 2nd Edition, Cold Spring Harbor Laboratory press (1989)), and other laboratory manuals. Additional examples of methods of introducing nucleic acid molecules encoding opsonins and/or opsonin/antigen complexes including an antigen and an opsonin are described below. The cells containing the introduced nucleic acid molecules encoding, for example, an opsonin, can themselves be administered to a subject (as the antigen) according to the methods of the invention, e.g., in a vaccine composition.

A. Introduction of Naked Nucleic Acid into Cells in vitro or ex vivo

1. Transfection mediated by $CaPO_4$: Naked nucleic acid can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in *Current Protocols in Molecular Biology*, Ausubel, F. M. et al. (eds.) Greene Publishing Associates, (1989), Section 9.1 and in *Molecular Cloning: A Laboratory Manual, 2nd Edition*, Sambrook et al. Cold Spring Harbor Laboratory Press, (1989), Sections 16.32–16.40 or other standard laboratory manuals.

2. Transfection mediated by DEAE-dextran: Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce nucleic acid transiently into cells but is not preferred for creating stably transfected cells. Thus, this method can be used for short term production of a gene product but is not a method of choice for long-term production of a gene product. Protocols for DEAE-dextran-mediated transfection can be found in *Current Protocols in Molecular Biology*, Ausubel, F. M. et al. (eds.) Greene Publishing Associates, (1989), Section 9.2 and in *Molecular Cloning: A Laboratory Manual, 2nd Edition.* Sambrook et al. Cold Spring Harbor Laboratory Press, (1989), Sections 16.41–16.46 or other standard laboratory manuals.

3. Electroporation: Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the nucleic acid and the ionic composition of the media. Electroporation can be used to stably (or transiently) transfect a wide variety of cell types and is only applicable to in vitro modification of cells. Protocols for electroporating cells can be found in *Current Protocols in Molecular Biology*, Ausubel, F. M. et al. (eds.) Greene Publishing Associates, (1989), Section 9.3 and in *Molecular Cloning: A Laboratory Manual. 2nd Edition*, Sambrook et al. Cold Spring Harbor Laboratory Press, (1989), Sections 16.54–16.55 or other standard laboratory manuals.

4. Liposome-mediated transfection ("lipofection"): Naked nucleic acid can be introduced into cells by mixing the nucleic acid with a liposome suspension containing cationic lipids. The nucleic acid/liposome complex is then incubated with cells. Liposome mediated transfection can be used to stably (or transiently) transfect cells in culture in vitro. Protocols can be found in *Current Protocols in Molecular Biology* Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157–176; Wang and Huang (1987) *Proc. Natl. Acad. Sci. USA* 84:7851–7855; Brigham et al. (1989) *Am. J Med. Sci.* 298:278; and Gould-Fogerite et al. (1989) *Gene* 84:429–438.

5. Direct Injection: Naked nucleic acid can be introduced into cells by directly injecting the nucleic acid into the cells. For an in vitro culture of cells, nucleic acid can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the nucleic acid is stably introduced into a fertilized oocyte which is then allowed to develop into an animal. The resultant animal contains cells carrying the nucleic acid introduced into the oocyte. Direct injection has also been used to introduce naked nucleic acid into cells in vivo (see e.g., Acsadi et al. (1991) *Nature* 332: 815–818; Wolff et al. (1990) *Science* 247:1465–1468). A delivery apparatus (e.g., a "gene gun") for injecting DNA into cells in vivo can be used. Such an apparatus is commercially available (e.g., from BioRad).

6. Receptor-Mediated DNA Uptake: Naked nucleic acid can also be introduced into cells by complexing the nucleic acid to a cation, such as polylysine, which is coupled to a ligand for a cell-surface receptor (see for example Wu, G. and Wu, C. H. (1988) *J Biol. Chem.* 263:14621; Wilson et al. (1992) *J Biol. Chem.* 267:963–967; and U.S. Pat. No. 5,166,320). Binding of the nucleic acid-ligand complex to the receptor facilitates uptake of the nucleic acid by receptor-mediated endocytosis. Receptors to which a nucleic acid-ligand complex have targeted include the transferrin receptor and the asialoglycoprotein receptor. A nucleic acid-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest.

Generally, when naked nucleic acid is introduced into cells in culture (e.g., by one of the transfection techniques described above) only a small fraction of cells (about 1 out of $10^5$) typically integrate the transfected nucleic acid into their genomes (i.e., the nucleic acid is maintained in the cell episomally). Thus, in order to identify cells which have taken up exogenous nucleic acid, it is advantageous to transfect nucleic acid encoding a selectable marker into the cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid.

B. Viral-Mediated Gene Transfer

A preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

1. Retroviruses: Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the, retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology,* Ausubel, F. M. et al. (eds.) Greene Publishing Associates, (1989), Sections 9.10–9.14 and other standard laboratory manuals. Examples of suitable retroviruses include pHJ, pZIP, pWE and pEM which are well known to those skilled in the art. Examples of suitable packaging virus lines include Crip, Cre, 2 and Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

2. Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral nucleic acid (and foreign DNA contained therein) is not integrated into the genome of a host cell but remains episomal, thereby avoiding potential problems that can occur as a result of insertional mutagenesis in situations where introduced nucleic acid becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J Virol.* 57:267). Most replication-defective adenoviral vectors currently in use are deleted for all or parts of the viral E1 and E3 genes but retain as much as 80% of the adenoviral genetic material.

3. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol Biol.* 7:349–356; Samulski et al. (1989) *J Virol.* 63:3822–3828; and McLaughlin et al. (1989) *J Virol.* 62:1963–1973). Vectors containing as little as 300 base pairs of AAV can be packaged and can integrate. Space for exogenous nucleic acid is limited to about 4.5 kb. An AAV vector such as that described in Tratschin et al. (1985) *Mol. Cell. Biol.* 5:3251–3260 can be used to introduce nucleic acid into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J Virol.* 51:611–619; and Flotte et al. (1993) *J Biol. Chem.* 268:3781–3790).

The efficacy of a particular expression vector system and method of introducing nucleic acid into a cell can be assessed by standard approaches routinely used in the art. For example, nucleic acid introduced into a cell can be detected by a filter hybridization technique (e.g., Southern blotting) and RNA produced by transcription of introduced nucleic acid can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate the efficacy of the system. Standard reporter genes used in the art include genes encoding b-glactosidase, chloramphenicol acetyl transferase, luciferase and human growth hormone.

A host cell of the invention, such as a prokaryotic or eukaryotic host cell in culture, can be used to produce (i.e., express) fusion polypeptides of the invention. Accordingly, the invention further provides methods for producing polypeptides of the invention using the host cells of the invention. In one embodiment, the method comprises culturing the host cell of invention (into which a recombinant expression vector encoding a polypeptide of the invention has been introduced) in a suitable medium until the polypeptide is produced. In another embodiment, the method further comprises isolating the polypeptide from the medium or the host cell.

Transgenic Animals

The host cells of the invention can also be used to produce nonhuman transgenic animals. For example, in one embodiment, a host cell of the invention is a fertilized oocyte or an embryonic stem cell into which nucleic acid molecules encoding molecules, e.g., polypeptides, of the invention have been introduced. Such host cells can then be used to create non-human transgenic animals in which exogenous nucleic acid molecules encoding the polypeptides of the invention have been introduced into their genome or homologous recombinant animals in which endogenous nucleic acid molecules have been altered. Such animals are useful for studying the function and/or activity of the molecules of the invention and for identifying and/or evaluating modulators of the activity of the molecules of the invention. As used herein, a "transgenic animal" is a non-human animal, preferably a mammal, more preferably a mouse, in which one or more of the cells of the animal includes a transgene. A transgene is exogenous nucleic acid which is integrated into the genome of a cell from which a transgenic animal develops and which remains in the genome of the mature animal, thereby directing the expression of an encoded gene product in one or more cell types or tissues of the transgenic animal.

A transgenic animal of the invention can be created by introducing nucleic acid molecules encoding the polypeptides of the invention into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of a polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the nucleic acid molecule of the invention, e.g., the transgene in its genome and/or expression of the transgene mRNA in tissues or cells of the animals. A transgenic founder animal can then be used to breed additional animals carrying the transgene. Moreover, transgenic animals carrying a transgene encoding polypeptides of the invention can further be bred to other transgenic animals carrying other transgenes.

Vaccine Compositions

Yet another aspect of the invention features vaccine compositions which include the nucleic acid molecules, the vectors containing the nucleic acid molecules, or the fusion polypeptides of the invention and a pharmaceutically acceptable carrier. These vaccine compositions can provide protection against (used as a prophylactic) infection by the antigen encoded by the nucleic acid molecule or included in the fusion polypeptide of the invention. In addition, the vaccine compositions of the invention can be used to treat (used as a therapeutic) infection by the antigen encoded by the nucleic acid molecule or included in the fusion polypeptide of the invention.

The preparation of vaccine compositions which contain the nucleic acid molecules or the fusion polypeptides of the invention as the active ingredient, is known to one skilled in the art. Typically, such vaccines are prepared as injectables, either as liquid solutions or suspensions; solid forms suitable for solution in, or suspension in, liquid prior to infection can also be prepared. The preparation can also be emulsified, or the protein encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP),N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-g, IL-2 and IL-12) or synthetic IFN-g inducers such as poly I:C can be used in combination with adjuvants described herein.

Dosage and Administration

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation can result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25–70%.

The nucleic acid molecules or fusion polypeptides of the invention can be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a preferred range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule, or preferably in a multiple dose schedule. A multiple dose schedule is one in which a primary course of vaccination can include 1–10 separate doses, followed by other doses given at subsequent time intervals required to maintain and or reinforce the immune response, for example, at 1–4 months for a second dose, and if needed, a subsequent dose(s) after several months. Periodic boosters at intervals of 1–5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-g released from the primed lymphocytes. The assays can be performed using conventional labels, such as radionucleotides, enzymes, fluorescent labels and the like. These techniques are known to one skilled in the art and can be found in U.S. Pat. Nos. 3,791,932, 4,174,384 and 3,949,064, which are hereby incorporated by reference.

Intramuscular Injection of Naked DNA

Naked DNA refers to DNA that is free from association with proteins or lipids that enhance introduction of the DNA into a host cell. For direct gene transfer of tibialis anterior (TA) muscle in mice, it is optimal to use 6–8 week old mice (weight 19–21 gm). Females give better immune responses for the hepatitis B surface antigen, and this might be true for some other antigens. The choice of mouse strain will also depend on the antigen. Mice should be anaesthetized since awake mice will contract their muscles and squeeze the DNA solution out. We use either sodium pentobarbital anesthesia (75 mg/kg IP) or halothane inhaled anesthetic (e.g. Metofane form Pittman-Moore). After the mice are asleep the hindlimbs are shaved to better reveal the tibial bone and the access to the TA muscle. Shaving off the limbs allows much greater precision and thus reproducibility for the actual injection step.

In preparation for the intramuscular injection, DNA is dissolved in endotoxin-free injectable PBS (not Tris EDTA) and is best at 0.1–2 mg/ml (depending on how immunogenic your protein is and how rapid a response you want).

To inject plasmid DNA use a 27GX¾" (0.4×20 mm) needle attached to a 1 ml tuberculin syringe. A piece of polyethylene tubing (PE 20, ID-0.38 mm) should be fit over the needle such that only 2–3 mm of needle protrudes (basically just the beveled portion should protrude). Fill the syringe with the DNA solution, attach the needle and then slowly fill the needle so that no air bubbles are trapped. The problem of dead volume is simplified using an insulin syringe (see below).

Alternatively, use a U-100 insulin syringe (1 cc or ³⁄₁₀ cc) which comes with a pre-attached 29G½ needle. Polyethylene tubing is used in the same way as described above. Inject through the skin—the tip of the needle should be about 3 mm lateral to the anterior tibial tuberosity (this is about half way between the knee and the ankle), keeping the needle almost perpendicular to the tibial. Once the needle is in place (push in until the end of the PE tubing rests against the skin with a bit of pressure), inject the 50 $\mu$l slowly (over approximately 10 sec), hold the needle in place for another 5–10 sec, then remove the needle slowly. If you accidentally pull the needle out before injection, try to reinsert it in the same hole, otherwise you will experience leakage.

Yet another aspect of the invention pertains to methods for modulating an immune response in an animal, e.g., a non-rodent animal, e.g., a non-rodent mammal, to an antigen. These methods include administering to the animal a nucleic acid molecule or a fusion polypeptide of the invention in an amount and over a period of time effective to modulate an immune response to the antigen in the animal. The term "modulate" as used herein refers to inhibition or activation/stimulation of an immune response to an antigen, a combination of an inhibition and an activation of an immune response (e.g., an inhibition of a humoral immune response and an activation of a cell mediated immune response or vice versa, or an inhibition of a systemic immune response and an activation of a secretory immune response or vice versa), or a change in the character of an immune response to an antigen. Assays are provided herein for determining immune response modulation.

Preferred direct targets of the compositions and methods of the invention include phagocytic leukocytes, e.g., cells of monocyte lineage. The term "non-rodent animal" as used herein refers to any animal which is not a rodent, e.g., a mouse or rat. The term "mammal" as used herein refers to a mammal, e.g., a non-rodent mammal. Examples of preferred mammals include domestic mammals kept for purposes of food production, labor, or companionship, and primates, e.g., humans.

The phrase "in an amount and over a period of time effective to modulate an immune response to the antigen in the mammal" refers to a dosage and period of time in which modulation of an immune response in the recipient mammal or recipient subject occurs. In one embodiment, such an immune response can be observed when the recipient subject exhibits, for example, increased resistance to a challenge by the antigen against which the subject has been immunized using the nucleic acid molecules or the fusion polypeptides of the invention. The nucleic acid molecules and the fusion polypeptides of the invention are typically administered to the recipient animal or subject in the form of a vaccine composition by the routes and in the formulations described herein. In addition, the nucleic acid molecules and the fusion polypeptides of the invention, alone or in the form of a vaccine composition, can be administered in combination with other substances which influence immune responses including, but not limited to, cytokines, anaphylatoxins, cell-death inducing molecules, and cell surface molecules.

Yet another aspect of the invention pertains to antibodies reactive with the fusion polypeptides of the invention. The term "antibody" as used herein refers to monoclonal and polyclonal antibodies. For example, by using the fusion polypeptides of the invention as immunogens, anti-the fusion polypeptide antisera or monoclonal antibodies can be made by standard protocols (See, for example, *Antibodies: A Laboratory Manual* ed. by Harlow and Lane (Cold Spring Harbor Press: 1988)).

Assays for Determining Immune Response Modulation According to the Invention

Fusion polypeptides and multichain complexes are useful according to the invention to modulate an immune response in a mammalian, preferably a human, to an antigen or antigens. The polypeptides or complexes are administered and are taken up (i.e., ingested or phagocytosed) by antigen presenting cells.

An "immune response" refers to stimulation/activation of a selected response involving the immune system, or suppression, elimination, or attenuation of a selected response. Thus, to modulate an immune response means that the desired response is more efficient, more rapid, greater in magnitude, and/or more easily induced than when a control protein is administered in an identical fashion.

The following in vitro and in vivo assays are useful for determining whether an immune response is modulated according to the invention. The assays described in detail below measure stimulation or suppression of cellular or humoral immune responses to an antigen. The antigens referred to in the following assays are representative. It will be apparent to one of skill in the art that an immune response to a selected antigen useful according to the invention may be measured using one or more of the following assays by adapting the assay to that antigen.

I. Detection of Increased Phagocytosis

The following assay may be used in order to determine whether fusion polypeptides or complexes stimulate phagocytosis by antigen presenting cells.

Phagocytosis is examined using monocytes that have been adhered at 37° for 30 min in RPMI without added FCS. Sheep erythrocytes are incubated with a candidate opsonin, or its precursor, under conditions such that there are no more than 300 of such molecules, on average, are deposited on each erythrocyte. If a precursor is used, coated erythrocytes are then processed to convert all precursors to the actual candidate opsonin molecule (e.g., See Carlo et al., *J Immunol* 123:523–8(1979)). Fresh monocytes are isolated from the subject, and $5\times10^4$–$1\times10^5$ of these cells suspended in 0.25–0.5 ml of RPMI medium with 1% BSA. This aliquot is placed in a tissue culture well and incubated for 30 min at 37° C. An excess of coated erythrocytes, suspended at $1.2\times10^8$ cells/ml, is overlain on the monocytes, the plate is centrifuged for 5 min at 50 g, and incubated for 30 min at 37° C. Non-ingested material is removed in two hypotonic lysis steps using ice-cold lysing buffer before fixing and staining the adherent cells, and examining the cells under light microscopy. Phagocytosis is quantified by determining the percentage of 100 monocytes ingesting one or more target cells, and the total number of ingested E/100 monocytes (PI) is recorded. Stimulation of phagocytosis according to the invention is indicated by a phagocytic index of equal to or greater than 40.

II. Amplification of the immune response usually involves proliferation of particular subpopulations of lymphoid cells that are normally in the resting state.

Proliferative assays have the following applications in clinical studies: (1) Assessment of overall immunologic competence of T cells or B cells as manifested in their ability to respond to polyclonal proliferation signals such as mitogens or anti-CD3 antibodies. Defects in the proliferation may be indicative of fundamental cellular immunologic defect. Low proliferation is often found as a nonspecific secondary effect of chronic disease. (2) Assessment: of an individual's response to specific antigens, where low responses are indicative of general or specific immunologic defect. (3) Determination of MHC compatibility by the mixed lymphocyte reaction (MLR).

In addition, proliferative assays are useful for estimating lymphokine production, investigating signal transduction, and assessing growth factor requirements (e.g., lymphokines) for T or B cells. The procedure outlined here measures incorporation of [$^3$H]thymidine into DNA, which usually correlates well with cell growth as measured by changes in cell number. However, when the activation stimulus is toxic, as with chemical activators such as ionomycin plus phorbol myristate acetate (PMA), the burst of new DNA synthesis following activation may not be accompanied with a net increase in viable cells, and, in fact, a decline in cell number may be observed. In this instance, [$^3$H]thymidine incorporation in DNA is more indicative of initial cell stimulation than estimation of cell number. In addition, [$^3$H]thymidine incorporation provides information on cell populations, not on individual cells. Alternate methods, such as flow cytometry may be used for studies requiring that type of information.

Assay For Antigen-Induced T Cell Proliferation

This protocol is designed to test the proliferation of T cells in response to a specific antigen—tetanus toxoid. It can be modified to test T cell proliferation in response to any protein or polysaccharide antigen. Materials: (T cell suspension, autologous antigen-presenting cell suspension (non-T cells), Tetanus toxoid solution (Connaught or State Laboratory Institute of Massachusetts)). (1) Count T cells and adjust to $1\times10^6$ cells/ml with complete RPMI-10 AB. (2) Treat antigen-presenting cells with mitomycin C (or irradiate with 2500 rad) as in step 2 of one-way MLR protocol. Adjust concentration of antigen-presenting cells to $2\times10^5$ cells/ml. Antigen-presenting cells can consist of autologous non-T cells or autologous monocytes/macrophages. (3) Add 100 ul T cell suspension and 50 ul antigen-presenting cell population to wells; mix just before dispensing. (4) Add 50 ul tetanus toxoid solution to give final concentrations of 0, 1, 5, 10, and 20 ug/ml. Prepare three wells for each dilution. (5) Incubate 6 days in a humidified 37° C., 5% $CO_2$ incubator. (6) Pulse with [$^3$H]thymidine and harvest as described in support protocol.

Assay For Lymphokine-Dependent Cell Proliferation

This protocol assays the lymphokine-dependent proliferation of a lymphocyte population, in this case, the IL-4 dependent proliferation of B cells. Materials: (Tonsil B cell suspension, Anti-IgM cross-linked to Sepharose beads (Bio-Rad), 10,000 U/ml human rIL-4 (Genzyme) in complete RPMI-10). (1) Count tonsil B cells and adjust concentration to $1\times10^6$ cells/ml with complete RPMI-10. (2) Dispense 100 ul of tonsil B cells into each well. Prepare three wells for each experimental condition. (3) Dilute 10,000 U/ml rIL-4 solution 1:10, 1:100, and 1:1000. Add 20 ul of the stock or dilution to appropriate wells to yield 1000 U/ml, 100 U/ml, 10 U/ml, and 1 U/ml. Include a control well with no rIL-4. (4) Pipet anti-IgM beads into appropriate wells.

Determine the optimal concentration of beads with pilot experiments. It is best to include several concentrations of beads in each experiment to "bracket" the optimal dose. Prepare wells with tonsil B cells and IL-4 dilutions alone, anti-IgM beads alone, culture medium alone, and all the combinations of IL-4 and anti-IgM bead dilutions. (5) Increase the volume of each well to 200 ul with complete RPMI-10 as necessary. (6) Culture 5 days in a humidified 37° C., 5% $CO_2$ incubator. (7) Pulse with [$^3$H]thymidine and harvest as described in support protocol.

[$^3$H]Thymidine Pulse And Harvest Of Cell Cultures

This protocol is used in conjunction with the preceding protocols to complete the [$^3$H] thyridine incorporation assay. (1) Add 20 ul of 50 uCi/ml [$^3$H]thymidine to each culture (1.0 uCi) at a fixed time before terminating the culture (usually 6 or 18 hr). (2) Harvest cell cultures using an automated multiwell harvester that aspirates cells, lyses cells, and transfers DNA onto filter paper, while allowing unincorporated [$^3$H]thymidine to wash out. Fill and aspirate each row of the microtiter plate ten times to ensure complete cell transfer and complete removal of unincorporated thymidine. Wash each filter strip with 100% ethanol to facilitate drying. Transfer to scintillation vials. For semiautomated harvester, transfer filter dots for each well into, scintillation counting vials. For manual transfer, dry filters under lamp and transfer to scintillation vial with forceps. Add scintillation fluid to each vial. (3) Count samples in scintillation counter until standard deviation is less than 2%. Calculate mean cpm for background cultures and for each experimental condition. There should be less than 20% variation in replicate cultures.

III. Induction And Measurement Of In Vitro Antibody Responses

The capacity of the human immune system to mount an antibody response following in vivo immunization with a protein or polysaccharide antigen is a revealing indication of the overall integrity of both the B and T cell arms of the immune system. As such, in vivo immunization followed by measurement of the antibody response is an appropriate test of immune function in the various acquired and congenital immunodeficiencies and in a host of other conditions affecting the immune system. The following procedures are for in vivo immunization and for the measurement of the subsequent immune response using an ELISA technique.

Immuno-Enzymetric Assay For Cytokines Using NIP- And HRPO-Labeled Antibodies

This protocol describes an immunonoenzymetric assay for cytokines using a heterogeneous, noncompetitive immunoassay reaction in which the cytokine is immobilized by a coating antibody bound to a microtiter plate. Unbound material is washed free, and detection is carried out using a different anti-cytokine antibody labeled with the hapten nitroiodophenyl (NIP). This is in turn detected by a horseradish peroxidase (HRPO) conjugate of an anti-NIP antibody, which is revealed with the chromogenic substrate ABTS. In this noncompetitive immunoassay, the immunoassay signal ($A_{405}$) increases as a direct function of the amount of cytokine present in the sample. Antibodies are prepared as described in Current Protocols in Immunology, 1995, 6.20.2–6.20.10.

Coat assay plate. (1) Using a multichannel pipettor, transfer 100 ul of an appropriate dilution of coating antibody into all wells of the assay plate that are to be used. (2) Seal plates with microtiter plate sealer or Parafilm and incubate 2 hr. At 37° C. Prepare samples and standards in preparation plate. (3) Dilute each sample (or aliquot of conditioned medium) to be assayed with an equal volume of immunoassay diluent. (4) Pipet less than or equal to 1 ml of each diluted sample to be assayed into the upper chamber of a separate Spin-X microfiltration device. Microcentifuge 5 min. At 10,000 rpm and save the filtrates that collect in the lower chambers. (5) Add 65 ul of each diluted sample to the appropriate well of a preparation plate (i.e., a separate 96-well microtiter plate). (6) Thaw an aliquot of cytokine standard at room temperature and make sure that it is well mixed. Pipet 130 ul into the well of the preparation plate representing the highest concentration on the standard curve. Transfer 65 ul from this well into the next, then continue performing serial 1:1 dilutions in immunoassay diluent so that 65 ul of each concentration represented on the standard curve is placed in appropriate well of the preparation plate. (7) Thaw an aliquot of calibrator at room temperature (if used). Dilute with an equal volume of immunoassay diluent, then pipet 65 ul of diluted calibrator into appropriate well or wells of preparation plate.

Incubate with coating antibody. (8) Remove coated assay plate from incubator. Dip in 2-liter beaker filled with 1×wash buffer, then invert over sink and flick to remove liquid. Repeat two more times, then bang dry on paper towel. (9) Transfer 50 ul of solution from each well of preparation plate to corresponding well of the assay plate using multichannel pipettor. (10) Seal plate with microtiter plate sealer or Parafilm and incubate 2 hr. at room temperature.

Incubate with detecting antibody. (11) Dilute NIP-labeled detecting antibody specific to cytokine of interest to 1 ug/ml in detecting buffer. (12) Wash assay plate as in step 8. (13) Add 75 ul diluted detecting antibody from step 11 to all wells of assay plate, including unused outer walls. (14) Reseal plate with microtiter plate sealer or Parafilm and incubate 1 hr. at room temperature.

Incubate with HRPO-conjugated anti-NIP antibody. (15) Dilute HRPO-conjugated anti-NIP Mab 1:3000 in detecting buffer. (16) Wash assay plate as in step 8. (17) Add 75 ul of diluted HRPO-labeled anti-NIP antibody from step 15 to all wells of assay plate. (18) Reseal plate with microtiter plate sealer or Parafilm and incubate 1 hr. at room temperature.

Incubate with chromogenic substrate. (19) Wash assay plate as in step 8. (20) Add 100 ul ABTS substrate working solutions to all wells of assay plate. Cover plate and incubate at room temperature until color development reaches desired level (generally until $A_{405}$ for wells containing the highest concentration of standard is between 1.5 and 2). This protocol usually produces an assay that can be read after 30 to 60 min.

Read plate and analyze data. (21) Using microtiter plate reader with computer interface, measure absorbance in all wells at 405 nm in single-wavelength mode or at 405 and 650 nm in dual-wavelength mode. (22) Fit standard data to a curve described by a first-degree (linear), second degree (quadratic), or four-parameter (nonlinear) mathematical function using curve-fitting software. (23) Interpolate absorbance data from unknown cytokine samples to fitted standard curve, and calculate cytokine concentrations.

IV. Induction of an in vivo antibody response provides an approach to the evaluation of the overall integrity of the immune system. In the protocols presented here, diptheria and tetanus toxoids are used as representative protein antigens and pneumococcal polysaccharides are used as representative polysaccharide antigens because of their safety and availability. It should be noted, however, that the responses elicited by these antigens are likely to be secondary responses because of past vaccination or natural exposure. To obtain a primary response, an unusual antigen such as keyhole limpet hemocyanin should be used.

When antigens are administered by the intramuscular or subcutaneous route, as they are here, a "systemic" immune response is induced and measurement of circulating antibody is most appropriate. It is, however, sometimes of interest to evaluate "local" or mucosal immune responses. In this case, the antigen is given either intranasally to stimulate respiratory lymphoid tissue or orally to stimulate gastrointestinal lymphoid tissue and bronchial washings or intestinal fluids, rather than blood, is assayed for antibody content; in addition, antigens are used that are more appropriate for stimulation of the local/mucosal response (i.e., influenza virus antigen for respiratory responses and cholera toxin for gastrointestinal responses).

In assaying the in vivo antibody response, it is important to determine responses to both protein and polysaccharide antigens because these antigens stimulate different components of the immune system. In this regard, the major antibody response to protein antigen is composed of IgG1 and IgG3 subclass antibodies, whereas the major antibody response to polysaccharide antigen is composed of IgG2 subclass antibody.

A variety of immunoassay techniques have been used to measure antibody responses in materials obtained after in vivo immunization. Of these, the ELISA assay is perhaps the most useful because it yields a stable, easily measurable, reproducible, and safe readout.

Induction Of In Vivo Antibody Responses To Protein/Polysaccharide Antigens

In this protocol antigens are administered by the intramuscular or subcutaneous route and serum is collected for measurement of responses. (1) Draw preimmunized blood sample, allow blood to clot, and separate serum from clot by centrifugation. Store serum at −20° C. to 70° C. in appropriately labeled plastic tubes. (2) Inject 0.5 ml of toxoid mixture into an appropriately prepared intramuscular site (deltoid or thigh), taking care not to inject material intravenously. (3) Inject 0.5 ml polyvalent pneumococcal vaccine into an appropriately prepared subcutaneous site, taking care not to inject material intravenously. (4) Draw post-immunization blood samples at desired intervals, usually at 1, 2, and 3 weeks. Separate serum and store at −20° C. to −70° C. (5) After all serum samples are collected, assay samples for presence of antibodies using ELISA.

The ELISA offers a rapid, sensitive, reproducible, nonradioactive method for measuring in vivo antibody responses to a variety of antigens, including protein and polysaccharide antigens in sera obtained from individuals vaccinated with tetanus and diphtheria boosters and the polyvalent pneumococcal polysaccharide vaccine. Assays specific for tetanus, diphtheria and the pneumococcal polysaccharide types I, II, and III are detailed in Current Protocols in Imnmunology, 1995, Vols. 6 and 7.

The invention is further illustrated by the following exemplification which in no way should be construed as being further limiting. The contents of all cited references (including literature references, issued patents, published patent applications, and co-pending patent applications) cited throughout this application are hereby expressly incorporated by reference.

EXEMPLIFICATIONS

Example 1

A fusion gene incorporating sequences for the pneumococcal antigen pneumolysin and for the alpha chain of the opsonin murine C3b is generated using the following method.

The sequence encoding the alpha chain of murine C3b is amplified by PCR from mouse liver cDNA using an upstream primer corresponding to nt 2301–2324 of Genbank K02782, and a downstream primer complementary to nt 5018–5045. The gene for pneumolysin is amplified from pneumococcal DNA using an upstream primer corresponding to nucleotides 207–233 of Genbank M17717 and flanked on the 5' end by 12 bases that correspond to nt 5034–5045 of Genbank K02782 and a downstream primer that corresponds to the sequence complementary to nucleotides 599–1622 of M17717 and flanked at the 5' end by a Sph I site. Both products are isolated by agarose gel electrophoresis, eluted using glass beads, and used, in equimolar amounts, in a PCR reaction with excess amounts of the upstream C3b alpha chain primer and the downstream pneumolysin primer. The fusion product is isolated by agarose gel electrophoresis and digested with Sph I. A double-stranded DNA sequence corresponding to the mouse IL-2 secretory sequence (nt 48–107 of Genbank X01772) and flanked upstream by a single-stranded Hind III overhang is prepared. The mammalian expression vector pcDNA3 is digested with Hind III and Sph I, and the fragments are ligated into the plasmid so that the CMV promoter is upstream of the IL-2 signal sequence, which is upstream of the C3b alpha chain/pneumolysin fusion gene.

Example 2

A fusion gene incorporating sequences for the pneumococcal antigen pneumolysin and for the opsonin murine C3 is generated using the following method.

The sequence encoding murine C3 is amplified by PCR from mouse liver cDNA using an upstream primer corresponding to nt 57–78 of Genbank K02782, and a downstream primer complementary to nt 5018–5045. The gene for pneumolysin is amplified from pneumococcal DNA using an upstream primer corresponding to nucleotides 207–233 of Genbank M17717 and flanked on the 5' end by 12 bases that correspond to nt 5034–5045 of Genbank K02782 and a downstream primer that corresponds to the sequence complementary to nucleotides 599–1622 of M17717 and flanked at the 5' end by a Sph I site. Both products are isolated by agarose gel electrophoresis, eluted using glass beads, and used, in equimolar amounts, in a PCR reaction with excess amounts of the upstream C3 primer and the downstream pneumolysin primer. The fusion product is isolated by agarose gel electrophoresis and digested with Sph I. The mammalian expression vector pcDNA3 is digested with Hind III, blunted with Klenow, and then digested with Sph I, and the fusion gene is ligated into the plasmid so that it is, downstream of the CMV promoter.

In Examples 1 and 2, fusion constructs comprising pneumolysin are useful for vaccinating an animal against infection with *S. pneumoniae*, e.g. pneumonia, meningitis, bacteremia, pericarditis, otitis media, or osteomyelitis. Efficacy of the vaccine, administered prophylactically or therapeutically, can be evidenced by a decreased incidence or prevalence of pneumococcal disease, a lower case-mortality rate, fewer complications, or a shorter mean duration of disease (e.g., reduction from 10 to 5 days) in a population.

Example 3

A fusion gene incorporating sequences for the antigen chicken lysozyme and for the opsonin murine mannose binding protein A (MBP) and for a $Gly_3$ linker is generated using the following method.

The sequence encoding MBP is amplified by PCR from mouse liver cDNA using an upstream primer corresponding to nt 121–142 of Genbank S42292 and a downstream primer complementary to nt 818–837 and flanked on its 5' side by 12 residues of poly-C. Lysozyme is amplified from chicken embryo cDNA using an upstream primer corresponding to nt 82–102 of Genbank V00428 and flanked on its 5' side by 12 residues of poly-G, which is itself flanked 5' by a sequence corresponding to nt 829–837 of S42292, and a downstream primer complementary to nt 450–468 of V00428 flanked on the 5' side by an Xba I site. Both products are isolated by agarose gel electrophoresis, eluted using glass beads, and used, in equimolar amounts, in a PCR reaction with excess amounts of the upstream MBP primer and the downstream lysozyme primer. The fusion product is isolated by agarose gel electrophoresis and digested with Xba I. The mammalian expression vector pcDNA3 is digested with Hind III, blunted with Klenow, and then digested with Xba I, and the fusion gene is ligated into the plasmid so that it is downstream of the CMV promoter.

Example 4

A fusion gene incorporating sequences for an immunodominant peptide of chicken lysozyme and for the opsonin murine mannose binding protein A (MBP) is generated using the following method.

The sequence encoding MBP is amplified by PCR from mouse liver cDNA using an upstream primer corresponding to nt 121–142 of Genbank S42292 and a downstream primer complementary to nt 818–837. A double-stranded oligonucleotide is obtained corresponding to nt 196–237 of Genbank V00428 and flanked on its downstream side by a single-stranded Xba I overhang. The pcDNA3 plasmid is digested with Hind III, blunted with Klenow, and digested XbaI. The MBP sequence is ligated to the vector and the product is isolated by agarose gel electrophoresis and glass beads elution. The lysozyme peptide encoding sequence is ligated into the latter product, and, using restriction digest analysis and DNA sequencing, clones are identified in which a single MBP gene in sense orientation is immediately downstream of the promoter and upstream of the lysozyme peptide gene.

Example 5

In this example, the APC binding domain is located at the carboxy terminus of the fusion polypeptide and the antigen is located at the amino terminus of the fusion polypeptide.

A fusion gene incorporating sequences for an immunodominant peptide of chicken lysozyme and for the APC binding moiety of the opsonin murine a2macroglobulin is generated using the following method.

The sequence encoding a2m is amplified by PCR from mouse liver cDNA using an upstream primer corresponding to nt 3683–3709 of Genbank M93264 and a downstream primer complementary to nt 4510–4537 and flanked on its 3' side by an Xho I site. A double-stranded oligonucleotide is obtained corresponding to nt 196–237 of Genbank V00428 and flanked on its downstream side by a sense-strand C paired with an antisense-strand G, followed by a sense-strand G paired with an antisense-strand C, followed by a sense-strand Apa I overhang. A double-stranded DNA molecule corresponding to the mouse IL-2 secretory sequence (nucleotides 48–107 of Genbank Acc. X01772) flanked upstream by a single-stranded HindIII overhang is prepared. The a2m fragment is digested with XhoI and ApaI. The pcDNA3 plasmid is digested with Hind III, and digested with XhoI. The three fragments are ligated into the vector.

In Examples 3–5, Chicken lysozyme is a well-characterized reporter antigen that can be used to evaluate the immunomodulatory effects of a fusion polypeptide comprising it. Animals can be vaccinated with the plasmid encoding the fusion polypeptide (or the polypeptide itself) or a plasmid encoding the antigen (or the antigen itself). The immune responses to the antigen can then be compared by assays for, e.g., antibody production, lymphocyte proliferation, cell-mediated cytotoxicity, or cytokine production. Another type of assay involves challenging the animals with syngeneic tumor cells transfected with a gene encoding the antigen and examining for a reduced incidence of tumor formation (e.g., from 80% to 40%) in animals receiving the fusion vaccine versus those receiving the antigen vaccine.

Example 6

In this example, the molecule comprises an antigen and two different opsonins. A fusion construct comprising the a2m APC binding site and an immunodominant peptide of chicken lysozyme is prepared in a manner similar to that of Example 5. The gene encoding murine MBP-A is then amplified in a manner that allows it to be ligated in-frame upstream of the lysozyme peptide. In this case, the MBP moiety provides a secretory signal for the entire fusion polypeptide, which can be inserted into an appropriate expression vector.

Example 7

In this example, three units of the same opsonin are included in one polypeptide. The sequence encoding the alphaAE chain of murine C3b is amplified in three ways: in one reaction, the downstream primer includes a sequence that can be annealed in-frame to the upstream end of the sequence obtained in a second reaction. The downstream end of the second sequence is designed to anneal in-frame to the upstream end of a sequence obtained in a third reaction. The downstream end of the third C3b alphaAE encoding sequence is designed to anneal in-frame to a sequence encoding a polypeptide chain of telomerase, a tumor antigen. The construct can be cloned into a secretory expression vector which places the murine IL-2 secretory sequence in-frame upstream of the first C3 b.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method of modulating in a mammal an immune response to an antigen, comprising administering to the mammal a nucleic acid molecule encoding a polypeptide comprising said antigen, a secretory sequence, and an amino acid sequence that binds to a cell surface molecule of an antigen presenting cell of monocytic lineage in an amount effective to modulate an immune response.

2. The method of claim 1 in which said amino acid sequence that binds to a cell surface molecule comprises an antigen presenting cell (APC) binding domain of an opsonin.

3. The method of claim 2 wherein said APC binding domain of said opsonin is a domain of an opsonin selected from the group of opsonins consisting of: Fibronectin, C3, a collectin, alpha-2 macroglobulin, C-reactive protein, complement component C1q, complement fragment C3b, complement component C4b, mannose binding protein, conglutinin, surfactant protein A, and surfactant protein D.

4. The method of claim 2 wherein said APC binding domain of an opsonin comprises an opsonin.

5. The method of claim 2 wherein said APC binding domain of an opsonin is a first APC binding domain of an opsonin and said polypeptide further comprises a second APC binding domain of an opsonin.

6. The method of claim 5 wherein said second APC binding domain of an opsonin is different from said first APC binding domain of an opsonin.

7. The method of claim 1, wherein said antigen is selected from the group consisting of: a bacterial antigen, a viral antigen, a tumor antigen, an antigen that is associated with an autoimmune disease, and an antigen that is associated with an allergy.

* * * * *